(12) United States Patent
Moshier et al.

(10) Patent No.: US 11,585,821 B2
(45) Date of Patent: Feb. 21, 2023

(54) METHODS FOR SAMPLE PREPARATION AND TESTING

(71) Applicant: Acumen Detection Inc., Syracuse, NY (US)

(72) Inventors: Timothy F. Moshier, Volney, NY (US); Kenton A. Doctor, East Syracuse, NY (US); Fathima F. Rinzan, Manlius, NY (US); Angelina Lumia, Camillus, NY (US); Deborah L. Plochocki, Marcellus, NY (US)

(73) Assignee: Acumen Detection Inc., Syracuse, NY (US)

( * ) Notice: Subject to any disclaimer, the term of this patent is extended or adjusted under 35 U.S.C. 154(b) by 310 days.

(21) Appl. No.: 16/728,229

(22) Filed: Dec. 27, 2019

(65) Prior Publication Data

US 2020/0209267 A1 Jul. 2, 2020

Related U.S. Application Data

(60) Provisional application No. 62/785,303, filed on Dec. 27, 2018.

(51) Int. Cl.
  *G01N 1/28* (2006.01)
  *G01N 35/00* (2006.01)
  *G01N 1/44* (2006.01)

(52) U.S. Cl.
  CPC ......... *G01N 35/00732* (2013.01); *G01N 1/28* (2013.01); *G01N 1/44* (2013.01);
  (Continued)

(58) Field of Classification Search
  CPC .......... G01N 2035/00752; G01N 2035/00346; G01N 1/44; G01N 1/28; G01N 35/00732;
  (Continued)

(56) References Cited

U.S. PATENT DOCUMENTS

| | | | |
|---|---|---|---|
| 2014/0098252 A1* | 4/2014 | Chang | G01N 35/00732 348/207.99 |
| 2016/0122752 A1* | 5/2016 | Blattman | C12Q 1/6816 506/2 |

(Continued)

OTHER PUBLICATIONS

Cell Biosciences, Inc. (2010). Alphaimager HP, EP and EC User Guide. Santa Clara, CA; Cell Biosciences, Inc. (Year: 2010).*

*Primary Examiner* — Samuel P Siefke
*Assistant Examiner* — Tingchen Shi
(74) *Attorney, Agent, or Firm* — George McGuire (57) ABSTRACT

A method and system for analyzing a sample potentially comprising a target, comprising: (i) activating one or more components of the sample analysis system in preparation for a sample, wherein the sample analysis system comprises a heating element, a centrifuge, a thermocycler, an imager, a user interface, and a processor; (ii) obtaining a sample potentially comprising a target; (iii) adding the obtained sample to a sample preparation receptacle, the sample preparation receptacle comprising one or more reagents configured to maximize success of the sample analysis; (iv) heating the sample preparation receptacle, with the added sample, in the heating element of the sample analysis system at a first temperature for a first heating period of time; (v) centrifuging the sample preparation receptacle, after heating, for a first period of time using the centrifuge of the sample analysis system; (vi) transferring at least a portion of the sample, after centrifugation, from the sample preparation receptacle to a sample analysis receptacle, the sample analysis receptacle comprising one or more reagents configured for a qPCR reaction specific to a selected target; (vii) obtaining, via the thermocycler and imager of the sample analysis system, a fluorescence curve during a qPCR reaction; (viii) analyzing, by the process of the sample analysis system, the obtained fluorescence curve to determine a (Continued)

presence or absence of the selected target in the sample; and (ix) reporting, to a user by the user interface of the sample analysis system, the presence or absence of the selected target in the sample; wherein one or more steps of the method are guided by interactive instructions provided by the sample analysis system.

10 Claims, 8 Drawing Sheets

(52) U.S. Cl.
CPC .............. *G01N 2035/00346* (2013.01); *G01N 2035/00752* (2013.01)

(58) Field of Classification Search
CPC .. G01N 35/00722; G01N 33/50; G01N 33/53; G01N 33/5306; C12Q 1/68; C12Q 1/6806; C12Q 1/6804; C12Q 1/6809; C12Q 2563/103; C12Q 2563/107
See application file for complete search history.

(56) References Cited

U.S. PATENT DOCUMENTS

| | | | |
|---|---|---|---|
| 2016/0319348 A1* | 11/2016 | Georgiou | C12Q 1/6869 |
| 2021/0155978 A1* | 5/2021 | Tidd | C12Q 1/6844 |

* cited by examiner

100

Activate the sample collection system in preparation for a sample
110

Obtain a sample potentially comprising a target
120

Add the obtained sample to a sample preparation receptacle
130

Heat the sample in the sample preparation receptacle
140

Centrifuge the sample in the sample preparation receptacle
150

Transfer sample to a second sample preparation receptacle
152

Transfer sample to a sample analysis receptacle
160

Analyze the sample via qPCR to obtain a fluorescence curve
170

Analyze fluorescence curve to determine presence or absence of target in the sample
180

Report the determination
190

METHODS FOR SAMPLE PREPARATION AND TESTING

CROSS-REFERENCE TO RELATED APPLICATION

The present application relates and claims priority to U.S. Provisional Application Ser. No. 62/785,303, filed Dec. 27, 2018, the entire contents of which are hereby incorporated by reference.

FIELD OF THE INVENTION

The present disclosure is directed generally to methods and systems for rapid, semi-automated sample preparation and testing.

BACKGROUND

The automation of sample preparation and testing is beneficial for many different reasons. First and perhaps foremost, automated or semi-automated sample preparation methods and systems can reduce or prevent human error. Human error can be a significant factor in poor sample preparation, inaccurate test results, misidentification and/or misdiagnosis, and other negative outcomes of sample preparation and testing. Second, automation or semi-automation may reduce costs by streamlining the sample preparation and testing process, by reducing errors that can significantly increase costs due to the long-term or enduring effects of misidentification and/or misdiagnosis, and by preventing duplicate sample analysis, among other possible cost-saving means. These and many other possible negative outcomes can be mitigated or prevented by automated or semi-automated sample preparation and testing.

Just one non-limiting example of sample preparation and testing is the analysis of milk. Dairy operations frequently test milk for a wide variety of reasons and applications. Milk testing requires accurate sample preparation and testing to prevent inconclusive results, misidentification and/or misdiagnosis issues, and other problems, all of which are expensive and time-consuming. Automating milk sample preparation and testing can prevent or mitigate against these expensive and time-consuming issues. Additionally, traditional milk sample analysis for pathogens can take 24 hours or longer to receive a diagnosis or other test results, a delay which is both time-consuming and expensive.

SUMMARY OF THE INVENTION

There is a continued need for sample preparation and analysis that minimizes cost, speeds the preparation and analysis process, and reduces the possibility of error. Automated and semi-automated processes can help achieve those goals.

The embodiments described herein are directed to methods and systems for rapid, semi-automated sample preparation and testing. A semi-automated testing system includes a computer comprising interactive instructions guiding the sample preparation and testing process, reagents for sample preparation and testing, and one or more components for sample testing including a heating element, a centrifuge, and a thermocycler with imager. The interactive instructions guide the user through the entire sample and analysis process using a series of prompts, timers, and other features. In addition, the system and method comprises a series of fail safes to ensure proper sampling and analysis.

According to an aspect is a method for analyzing a sample using a sample analysis system, comprising: activating one or more components of the sample analysis system in preparation for a sample, wherein the sample analyses system comprises a heating element, a centrifuge, a thermocycler, an imager, a user interface, and a processor; obtaining (a sample potentially comprising a target; adding the obtained sample to a sample preparation receptacle; heating the sample preparation receptacle, with the added sample, in the heating element of the sample analysis system at a first temperature for a first heating period of time; centrifuging the sample preparation receptacle, after heating, for a first period of time using the centrifuge of the sample analysis system; transferring at least a portion of the sample, after centrifugation, from the sample preparation receptacle to a sample analysis receptacle, the sample analysis receptacle comprising one or more reagents configured for a quantitative polymerase chain reaction specific to a selected target; obtaining, via the thermocycler and imager of the sample analysis system, a fluorescence curve during a quantitative polymerase chain reaction; analyzing, by the processor of the sample analysis system, the obtained fluorescence curve to determine a presence or absence of the selected target in the sample; and reporting, to a user by the user interface of the sample analysis system, the presence or absence of the selected target in the sample; wherein one or more steps of the method are guided by interactive instructions provided to the user via the user interface sample analysis system.

According to an embodiment, the sample preparation receptacle comprises one or more reagents configured to maximize success of the sample analysis.

According to an embodiment, the method further comprises the step of transferring a portion of the sample from the sample preparation receptacle to a reagent-containing tube and mixing to remove additional polymerase chain reaction inhibitors.

According to an embodiment, the instructions comprise a video that demonstrates the action that should be taken by the user.

According to an aspect is a system for analyzing a sample potentially comprising a target, comprising: a sample preparation receptacle; a heating element configured to heat the sample preparation receptacle, into which sample has been added, at a first temperature for a first heating period of time; a centrifuge configured to centrifuge the sample preparation receptacle, after heating, for a first period of time; a sample analysis receptacle comprising one or more reagents configured for a quantitative polymerase chain reaction specific to a selected target, into which sample from the sample preparation receptacle has been added after centrifugation; a thermocycler and imager configured to obtain a fluorescence curve during a quantitative polymerase chain reaction using the sample analysis receptacle; and a processor configured to: (i) analyze the obtained fluorescence curve to determine a presence or absence of the selected target in the sample; and (ii) report, via a user interface of the system, the presence or absence of the selected target in the sample; wherein the processor is further configured to provide guiding interactive instructions to the user, via the user interface, for one or more steps of the analysis.

According to an embodiment, the sample preparation receptacle comprises one or more reagents configured to maximize success of the sample analysis.

According to an embodiment, the system further comprises a memory configured for storing information.

According to an embodiment, the system further comprises a reagent-containing tube that a portion of the sample is added to and mixed to further sequester polymerase chain reaction inhibitors.

According to an embodiment, the system for analyzing a sample is a mobile system, such that all components are easily transferrable from one location to another.

According to an embodiment, the system further comprises a scanner.

According to an embodiment the sample preparation receptacle comprises a barcode.

According to an embodiment, the sample analysis receptacle comprises a barcode.

According to an aspect is a method for analyzing a sample using a sample analysis system, comprising: activating one or more components of the sample analysis system in preparation for a sample, wherein the sample analyses system comprises a heating element, a centrifuge, a thermocycler, an imager, a user interface, a processor; and a memory; obtaining a sample potentially comprising a target and providing the system with information about the sample which is stored in the memory; adding the obtained sample to a sample preparation receptacle and providing the system with information about the sample analysis receptacle which is stored in the memory; heating the sample preparation receptacle, with the added sample, in the heating element of the sample analysis system at a first temperature for a first heating period of time; centrifuging the sample preparation receptacle, after heating, for a first period of time using the centrifuge of the sample analysis system; transferring at least a portion of the sample, after centrifugation, from the sample preparation receptacle to a sample analysis receptacle, the sample analysis receptacle comprising one or more reagents configured for a quantitative polymerase chain reaction specific to a selected target, and providing the system with information about the sample analysis receptacle which is stored in the memory; cycling via thermocycler, wherein the identification of the sample analysis receptacle is recalled from the memory and used to determine directions for the polymerase chain reaction program; obtaining, via the thermocycler and imager of the sample analysis system, a fluorescence curve during a quantitative polymerase chain reaction; analyzing, by the processor of the sample analysis system, the obtained fluorescence curve to determine a presence or absence of the selected target in the sample; and reporting, to a user by the user interface of the sample analysis system, the presence or absence of the selected target in the sample; wherein one or more steps of the method are guided by interactive instructions provided to the user via the user interface sample analysis system.

According to an embodiment, the sample preparation receptacle comprises one or more reagents configured to maximize success of the sample analysis.

According to an embodiment, the method further comprises the step of transferring a portion of the sample from the sample preparation receptacle to a reagent-containing tube and mixing to remove additional polymerase chain reaction inhibitors.

According to an embodiment, the instructions comprise a video that demonstrates the action that should be taken by the user.

According to an embodiment, information about the sample preparation receptacle and the sample analysis receptacle is provided system via a scanner.

According to an embodiment, the sample preparation receptacle comprises a barcode containing information about the receptacle.

According to an embodiment, the sample analysis receptacle comprises a barcode containing information about the receptacle.

These and other aspects of the invention will be apparent from reference to the embodiment(s) described hereinafter.

BRIEF DESCRIPTION OF THE DRAWINGS

In the drawings, like reference characters refer to the same parts throughout the different views, and the drawings are not necessarily to scale.

DETAILED DESCRIPTION OF EMBODIMENTS

The present disclosure describes a semi-automated testing system with a computer comprising interactive instructions guiding the sample preparation and testing process, reagents for sample preparation and testing, and one or more components for sample testing including a heating element, a centrifuge, and a thermocycler with imager. The interactive instructions guide the user through the entire sample and analysis process using a series of prompts, timers, and other features. In addition, the system and method comprises a series of fail safes to ensure proper sampling and analysis.

Figure 1:
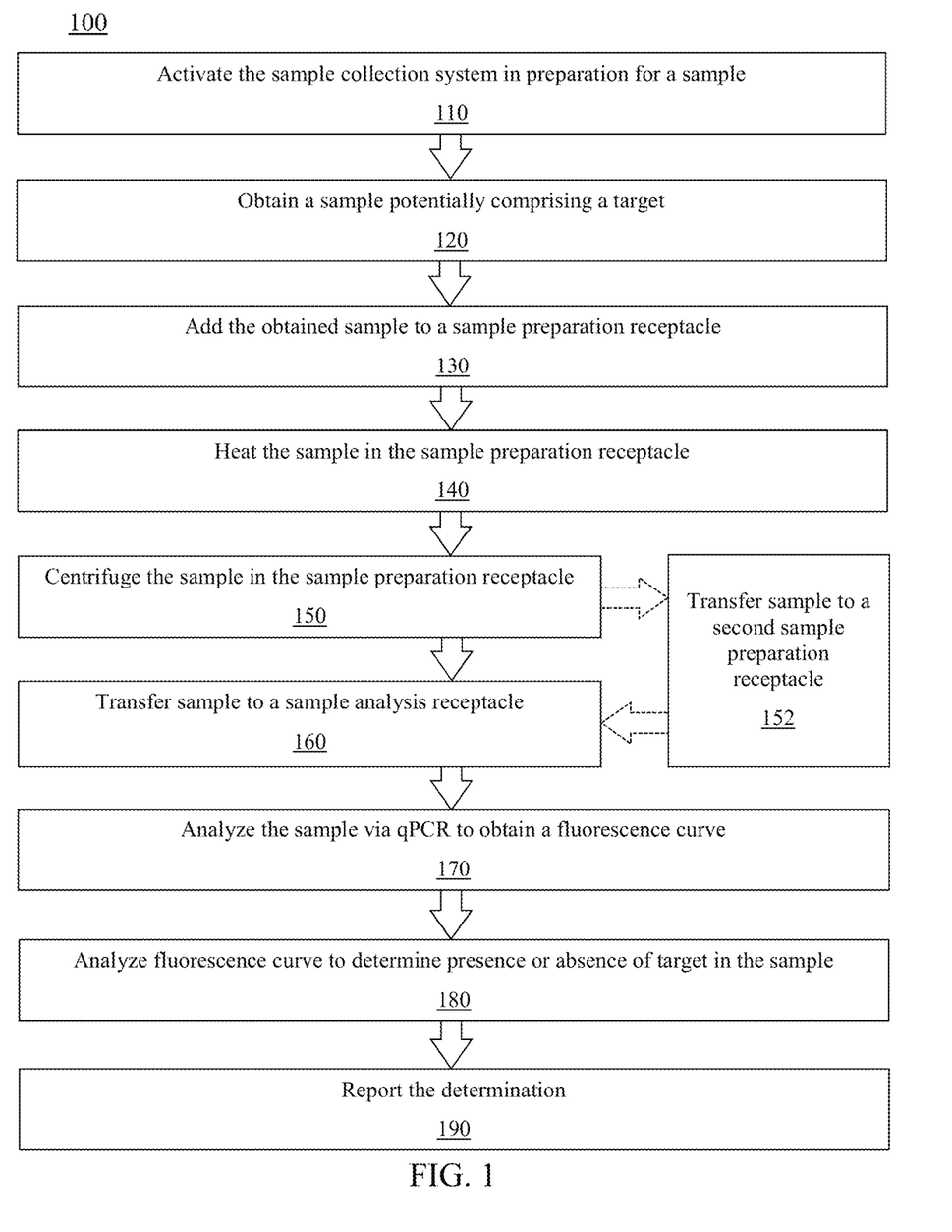
FIG. 1 is a schematic representation of a method for sample preparation and testing, in accordance with an embodiment.

Referring to FIG. 1, in one embodiment, is a flowchart of a method 100 for semi-automated sample preparation and testing using a computerized sample analysis system. The system can be any of the systems described or otherwise envisioned herein. For example, the system may include a computer with interactive instructions guiding a sample preparation and testing process, reagents for sample preparation and testing, and one or more components for sample testing including a heating element, a centrifuge, and a thermocycler with imager. These and many other components are possible components of the computerized sample analysis system. The computerized sample analysis system may be permanently or semi-permanently installed or affixed in a location, or the system may be mobile from one location to another. For example, the system may be a device that can be carried by a person from location to location, among many other embodiments.

At step 110 of the method, one or more components of the computerized sample analysis system are activated in preparation for a sample. For example, activation may comprise activating or engaging the interactive instructions for sample preparation and testing. The instructions may be embodied on a computer, such as a software program, that facilitates sample gathering, and other steps, by a user. The system may be activated in any of a wide variety of different ways, including turning on a computer or system, activating software, and/or any other method. For example, the computerized sample analysis system may be activated by engaging a software program configured to guide the user through sample collection and analysis.

Figure 2:
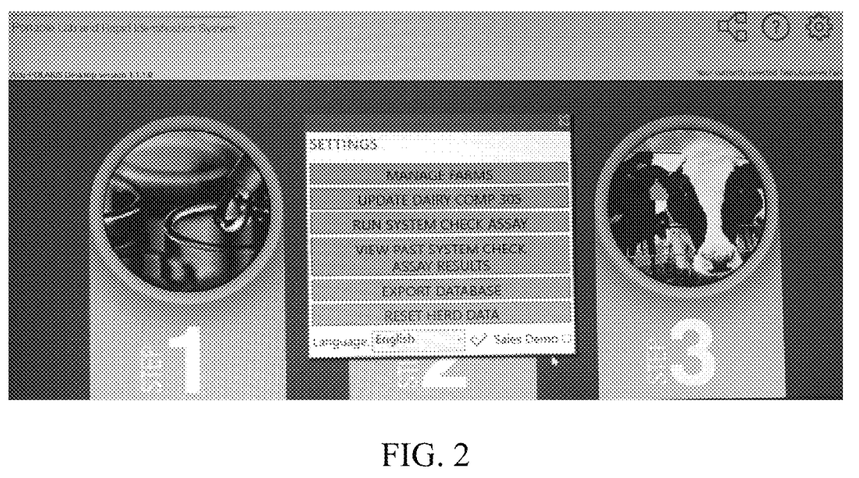
FIG. 2 is a schematic representation of a computerized interactive element of the testing system, in accordance with an embodiment.

Referring to FIG. 2, in one non-limiting embodiment, is an example of interactive instructions for a computerized sample analysis system. The software program has been activated and is ready for use. According to one possible embodiment, the program comprises numerous options in addition to the interactive sample collection and analysis guidance system. For example, as shown in FIG. 2, the system comprises functionality such as farm management, system updating, system analysis, database export, herd data, and more.

Figure 3:
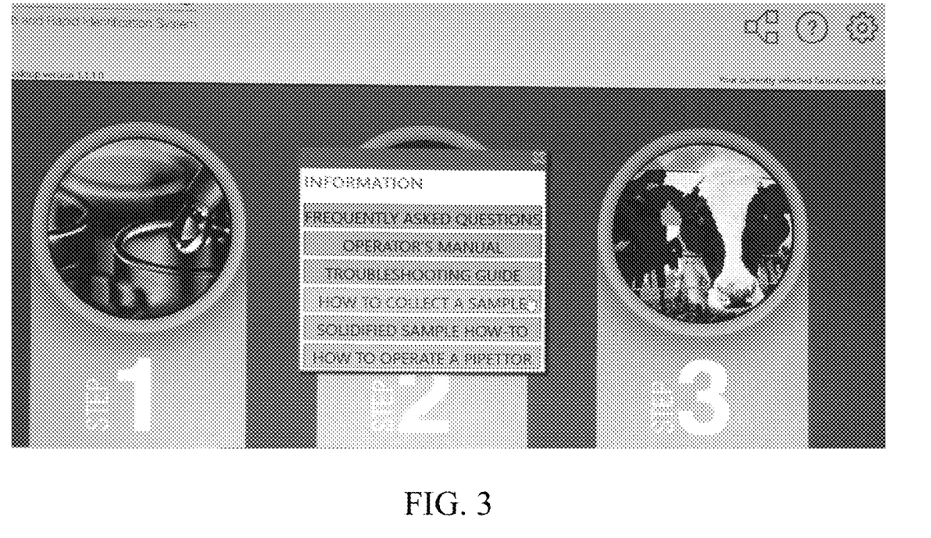
FIG. 3 is a schematic representation of a computerized interactive element of the testing system, in accordance with an embodiment.

Similarly, as shown in FIG. 3, in one embodiment, the software program may comprise information and/or help to further facilitate sample collection and analysis. For example, as shown in FIG. 3, the system comprises a Frequently Asked Questions (FAQ) section with information about the system, an Operator's Manual with detailed instructions about how to operate the system and software, a Troubleshooting Guide with information about how to resolve or address problems that might be encountered, instructions on how to collect a sample, instructions on how to analyze particular samples, and instructions on how to operate a pipettor, among many other possible instructions and information.

Figure 4:
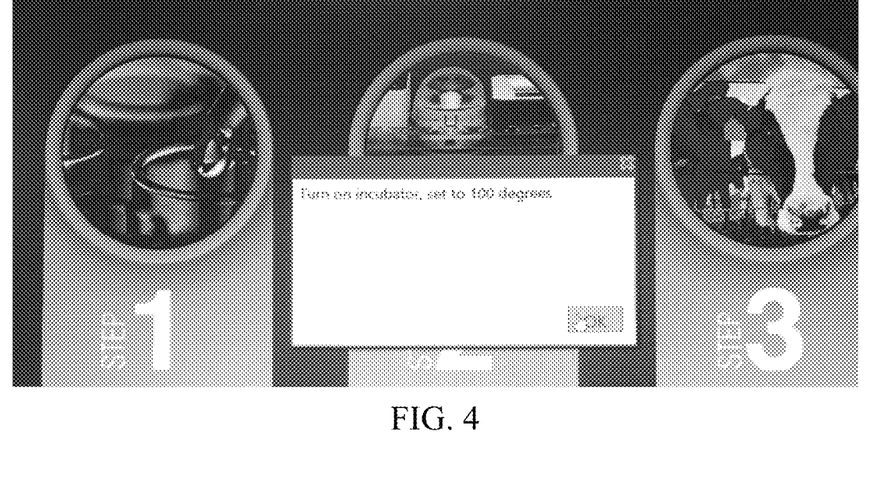
FIG. 4 is a schematic representation of a computerized interactive element of the testing system, in accordance with an embodiment.

The software program may further facilitate sample collection and analysis by providing additional directions for system setup or activation. Accordingly, the software program can direct the user to activate, modify, or otherwise interact with one or more components to prepare the system for sample analysis. For example, referring to FIG. 4 in one embodiment is an instruction to turn on the incubator and set it to a specific temperature (which can vary). Once this step has been performed by the user, the user can so indicate to the system (such as by clicking OK or otherwise informing the system) or the system can detect completion of the step, and then the system may proceed to a next step or indicate that the system is ready for a sample.

Although the accompanying figures depict an embodiment of one or more portions of a computerized sample analysis system, it is recognized that these are non-limiting embodiments and thus are exemplary embodiments only. Accordingly, the software program or other interactive instructions for a computerized sample analysis system will vary depending upon the configuration, programming, and/or settings of the system.

At step 120 of the method, a sample is obtained. The sample can be any sample capable of being analyzed by the system. Accordingly, the appropriate or possible samples may depend on the settings, configuration, and/or other parameters of the system. The system may comprise a target to be analyzed, such as for identification and/or quantification. The target may be a desired component or an undesired component of the sample. For example, the system may be configured to identify one or more elements expected to be found within the sample. As another example, the system may be configured to identify one or more elements which are not expected, or not desired, to be found within the sample. The target therefore may be anything that can be detected by analysis.

According to one non-limiting embodiment, the system is configured to analyze a body fluid from an organism. One example of analyzing a body fluid from an organism is analyzing a sample of milk obtained from a mammal either directly or indirectly. The mammal may be any mammal from which milk is obtained. For example, a sample of milk can be obtained from a single mammal or from a pool of milk from multiple mammals. When obtained from a single mammal, the sample may be obtained from a single teat or pooled from multiple teats. The sample of milk can then be analyzed using the system as described herein for desired components and/or for undesired components. As just one example, undesired components may include pathogens and/or contaminants, although many other components are possible. Accordingly, the computerized sample analysis system may be a device or components installed in a barn setting where milk samples can be quickly obtained and analyzed. Alternatively, the computerized sample analysis system may be a mobile device which is carried from one farm to another by a veterinarian, testing specialist, or other individual. These and many other examples and samples can be examined by the system described or otherwise envisioned herein.

Figure 5:
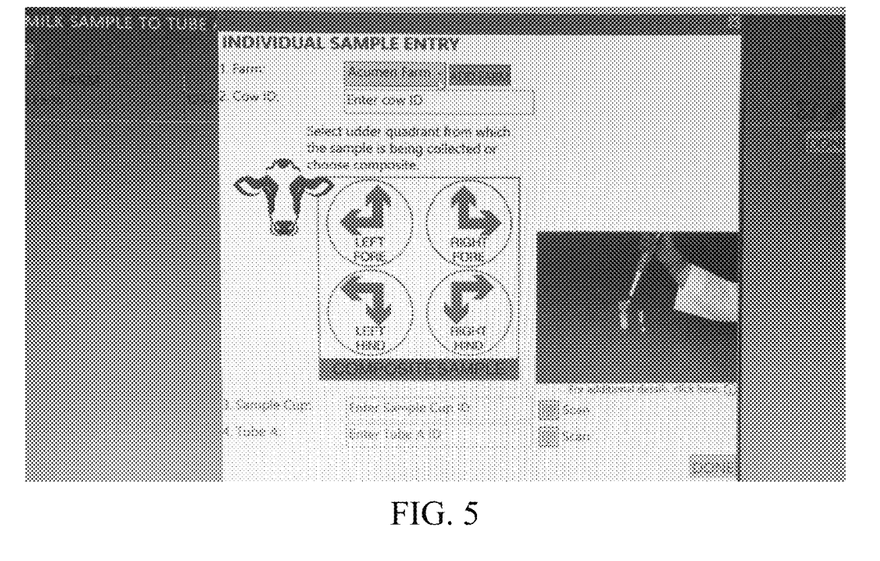
FIG. 5 is a schematic representation of a computerized interactive element of the testing system, in accordance with an embodiment.

Referring to FIG. 5, in one embodiment, is an image from the interactive software program of the system in which information about the sample is provided to the system for tracking and/or other purposes. In this example embodiment, the user provides the following information, although many other types of information may be obtained or provided:

1. Farm: an identification of the facility, and/or an option to add a new facility. In this example, there may be multiple facilities from which to select. This may be omitted or there may be no selection possible if the system is permanently installed at a location.
2. Cow ID: an identification of the source of the sample. In this example, the source of the sample is a cow, which will be associated with an identification that can be used for animal tracking. The cow may be associated with an identifier such as a number or other unique ID string that is obtained via RFID, an ear tag, or other source. This may be manually or automatically entered into the field. For example, according to an embodiment, the unique ID string is automatically populated when the system detects a nearby RFID tag or other source identification method. Since the source of the sample in this example is a cow, the cow ID includes an identification of one or more quarters (teats) from which the sample will be collected (left fore, right fore, left hind, and/or right hind). Accordingly, a sample may be collected from one quarter or may be a composite sample gathered from multiple quarters.
3. Sample Cup/Receptacle: an identification of the receptacle, such as a cup, into which the sample has been or will be collected. Since less than all of a collected sample is typically utilized for analysis, the sample receptacle is typically larger than the sample preparation receptacle used for downstream analysis. The identification of the receptacle may be a barcode or other unique ID string that is associated with a single receptacle. For example, a cup may be labeled with a sticker comprising the barcode or unique ID string, or may be imprinted with the information. The barcode or other unique ID string may be entered by scanning with an attached scanner, by a smartphone app, or by any other data entry mechanism.

4. Tube A: an identification of the sample preparation receptacle that the sample is added to (and which is obtained from the collection cup/receptacle). The sample preparation receptacle is described in greater detail below. The identification of the sample preparation receptacle may be a barcode or other unique ID string that is associated with a single sample preparation receptacle. For example, a tube may be labeled with a sticker comprising the barcode or unique ID string, or may be imprinted with the information. The barcode or other unique ID string may be entered by scanning with an attached scanner, by a smartphone app, or by any other data entry mechanism.

The system may be designed or configured to require or receive more or less information, and this may be determined by programming and/or by one or more settings of the system. For example, the source of the sample or one or more other inputs may determine what information should be or must be collected by the system.

Figure 6:
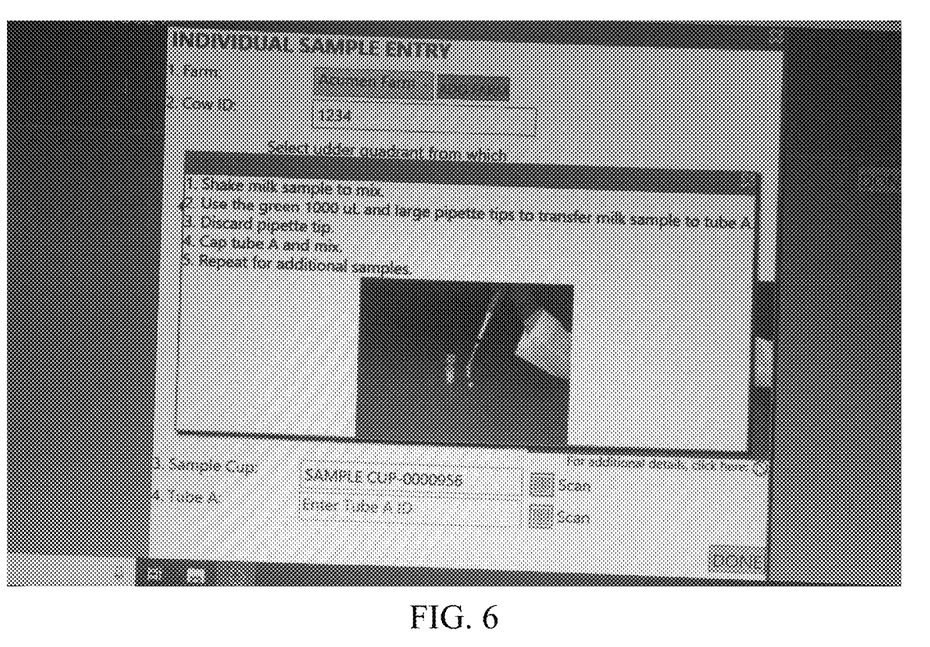
FIG. 6 is a schematic representation of a computerized interactive element of the testing system, in accordance with an embodiment.

Referring again to FIG. 5 is an interactive element of the system, specifically the image labeled "For additional details, click here." Clicking the help icon and/or the image produces an instructive pop-up or other source of instructions, such as that shown in FIG. 6, according to an embodiment. The instructions may comprise a gif or video that demonstrates the action that should be taken by the user. In this example, the instructions instruct the user to:

1. Shake the sample ("Shake milk sample to mix");
2. Add sample to the collection cup ("Use the green 1000 μl pipettor and large pipette tips to transfer milk sample to tube A," and "discard pipette tip");
3. Cap the sample preparation receptacle ("Cap tube A and mix");
4. Repeat if necessary ("Repeat for additional samples").

Accordingly, the gif or video might complete one or more of these steps. The system may be designed or configured to provide more or fewer instructions, and this may be determined by programming and/or by one or more settings of the system. Once the user has completed the steps, or is finished with the instructions, the user can engage the system to close the window and/or proceed to the next step.

Figure 7:
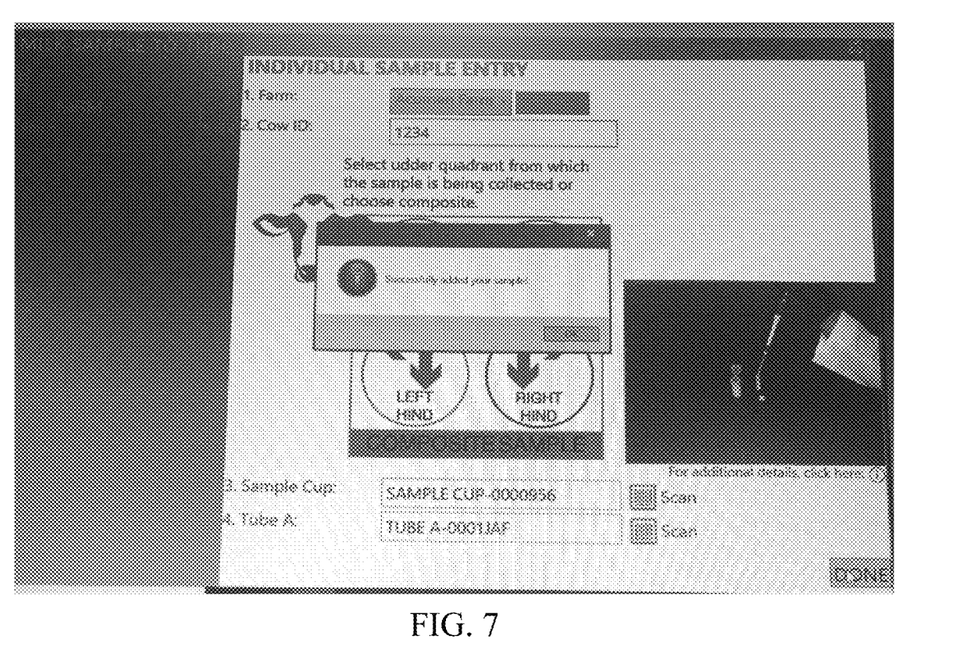
FIG. 7 is a schematic representation of a computerized interactive element of the testing system, in accordance with an embodiment.

Once the information has been entered and the sample has been collected, the user can engage the system to proceed to the next step or otherwise proceed to a downstream step of the system, such as by clicking "DONE" as shown in FIG. 7. This may produce a pop-up or other indication, for example, showing that the information about the collected sample has been successfully added to and recorded in the system. The system may therefore comprise a database storing information about the facility, the animals, and all other information associated with the samples.

Accordingly, at step 130 of the method the sample is added to a sample preparation receptacle, optionally comprising one or more reagents. The sample preparation receptacle can be any container sufficient to receive the sample, such as a tube, vial, vessel, container, or any other receptacle. The one or more reagents may be any reagents useful to prepare the sample for genomic analysis, including potentially maximizing PCR success and/or minimizing PCR inhibition. For example, the reagents may chelate and precipitate molecules that interfere with PCR.

According to an embodiment, the one or more reagents are lyophilized or otherwise processed or configured to enable storage, preferably for a long period of time and preferably at room temperature and/or a range of different temperatures that the receptacles may be expected to encounter. Accordingly, adding the sample to the lyophilized reagents will hydrate the reagents and allow them to interact with the sample.

According to an embodiment, the amount of the sample added to a sample preparation receptacle is a fixed amount, or a variable amount potentially comprising a minimum and/or maximum amount. For example, as shown in FIG. 6, the pipettor is used to transfer 1000 μl of the sample to the sample preparation receptacle, specifically Tube A with reagents.

At step 140 of the method the one or more sample preparation receptacles, each comprising a sample, is heated for a first period of time. Heating the sample lowers PCR inhibition and/or opens cells such as bacteria to allow access to genetic material. Indeed, heating produces an unexpected improvement in genetic analysis according to this method and system. The samples may be heated using any mechanism or device suitable to transfer heat to the receptacles, such as a heating block. According to an embodiment, the sample may be heated at approximately 100° C. in the heating block or other heating element for approximately 20 minutes, although a variety of temperatures for various amounts of time are possible.

Figure 8:
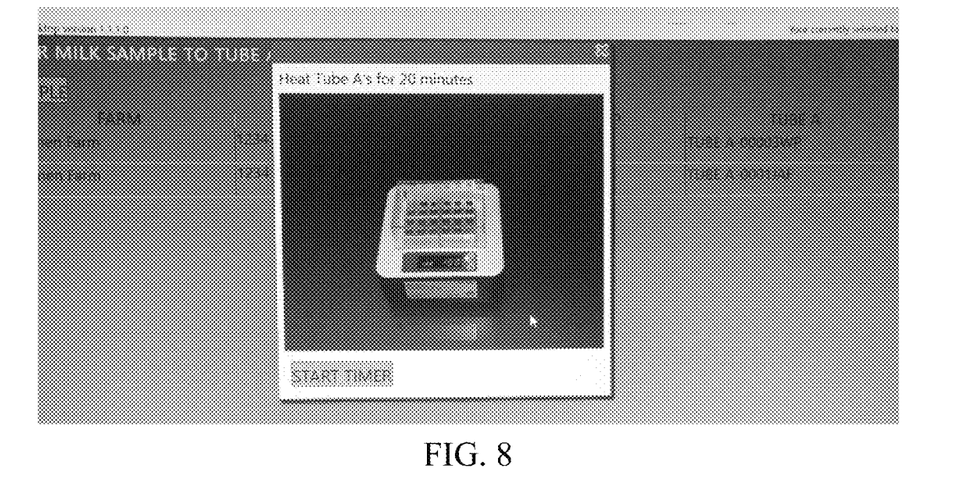
FIG. 8 is a schematic representation of a computerized interactive element of the testing system, in accordance with an embodiment.

According to an embodiment, the interactive instructions guide the user through the heating process. Referring to FIG. 8 is a non-limiting example of a pop-up showing instructions to heat the one or more sample preparation receptacles ("Tube A") at 100° C. in the heating block (an example is shown in the pop-up) for 20 minutes. By clicking on "START TIMER," a 20-minute timer will commence. When the timer is finished, the system may provide an alert, which may be visual, audible, or any other notification method.

At step 150 of the method, the sample is centrifuged or otherwise exposed to a centrifugal force for a first time period to remove large solids from the suspension. The centrifugal force and the first time period can be designed or selected to maximize successful downstream analysis of the sample. For example, the first time period can be approximately 10 seconds, although many other time periods are possible.

According to an embodiment, the sample is prepared for centrifugation by one or more of: (1) removing the sample preparation receptacle from the heating element and allowing the sample to cool for approximately one or more minutes and/or (2) inverting the sample preparation receptacle one or more times. Other steps may be used to prepare the sample for centrifugation.

Figure 9:
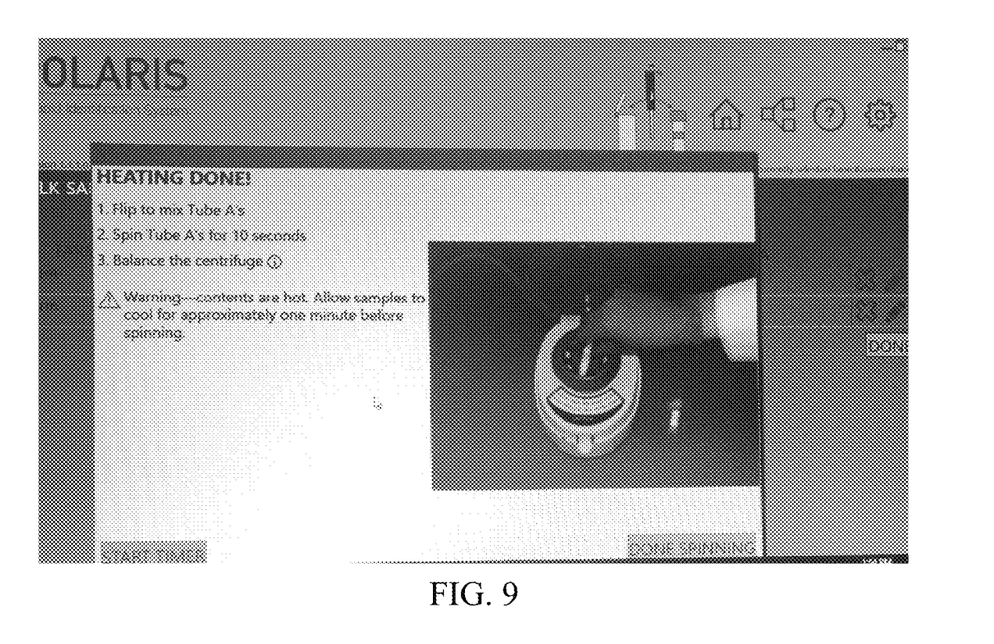
FIG. 9 is a schematic representation of a computerized interactive element of the testing system, in accordance with an embodiment.

According to an embodiment, the interactive instructions guide the user through the centrifugation process. Referring to FIG. 9 is a non-limiting example of a pop-up showing instructions to prepare the sample preparation receptacles ("Tube A") for centrifugation. The instructions inform the user to invert the sample preparation receptacle ("Flip to mix Tube A's"), to balance the centrifuge, and to spin the sample preparation receptacle for 10 seconds in the centrifuge.

Figure 10:
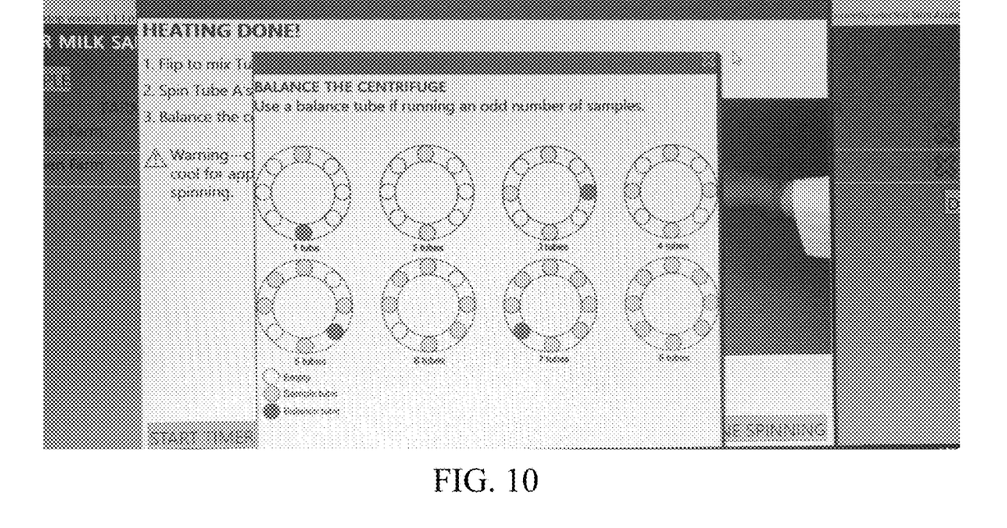
FIG. 10 is a schematic representation of a computerized interactive element of the testing system, in accordance with an embodiment.

The instructions inform the user to properly balance the centrifuge, and comprise additional help instructions as indicated by the "i" in a circle next to "Balance the centrifuge." Clicking the "i" in a circle produces a pop-up with the additional help instructions, as shown in FIG. 10. The figure shows a method for balancing one or more sample preparation receptacles in the centrifuge using a combination of empty slots, sample preparation receptacle(s), and/or a balance tube configured to balance with a properly-prepared sample preparation receptacle.

Once the centrifuge is properly balanced with the one or more sample preparation receptacles, the user can click or otherwise activate "START TIMER" to begin the 10-second timer, while simultaneously or near-simultaneously activating the centrifuge. When the timer is complete the user can deactivate the centrifuge, or it can be automatically deactivated. The user can then advance the system to the next step by clicking "DONE SPINNING."

At step 160 of the method, a portion of the sample from the sample preparation receptacle is transferred to a sample analysis receptacle. The transfer amount can be designed or selected to maximize successful downstream analysis of the sample. According to an embodiment, the transfer amount is a fixed amount, or a variable amount potentially comprising a minimum and/or maximum amount. For example, the amount can be approximately 200 µl, although many other amounts are possible.

In the current milk processing procedure we have a second tube containing reagents, Tube B, that further sequesters inhibitory materials that may be in the sample. The 200 µL from Tube A is transferred to Tube B and mixed. However, not all sample preparation procedures require this second tube. For example, our Colostrum Prep Kit uses only one tube, but is heated for 40 minutes at 75° C. From this step (whether it's the Tube B of the Milk Prep Kit, or the single tube from the Colostrum Prep Kit) 100 µL of liquid is transferred to the sample analysis receptacle (assay tube) for analysis/testing.

The sample analysis receptacle may optionally comprise one or more reagents, which can simply and speed the process since the user does not need the time or skill necessary to accurately measure out and add reagents to the sample analysis receptacle. The sample analysis receptacle can be any container sufficient to receive the sample, such as a tube, vial, vessel, container, or any other receptacle. The one or more reagents may be any reagents useful to prepare the sample for genomic analysis, including potentially maximizing PCR success and/or minimizing PCR inhibition.

According to an embodiment, the one or more reagents are lyophilized or otherwise processed or configured to enable storage, preferably for a long period of time and preferably at room temperature and/or a range of different temperatures that the receptacles may be expected to encounter. Accordingly, adding the sample to the lyophilized reagents will hydrate the reagents and allow them to interact with the sample.

According to an embodiment, the interactive instructions guide the user through the sample transfer process. For example, the instructions can direct the user to provide an identification of the sample analysis receptacle. The identification of the sample analysis receptacle may be a barcode or other unique ID string that is associated with a single receptacle. For example, the receptacle may be labeled with a sticker comprising the barcode or unique ID string, or may be imprinted with the information. The barcode or other unique ID string may be entered by scanning with an attached scanner, by a smartphone app, or by any other data entry mechanism.

As described here, the identification of the sample analysis receptacle provides important information to the analysis system. The sample analysis receptacle informs the system about which type of target is being sought in the sample, and thus informs the system about which PCR program to run, about how to interpret the results of the PCR amplification, and how to report the interpretation to the user, among other possible uses of the information.

The instructions can also direct the user to use a specific pipettor or other transfer device to move sample from the sample preparation receptacle is transferred to a sample analysis receptacle (e.g., "Use the 100 µl pipettor to transfer sample from Tube B to Assay Tube," and "discard pipette tip"). The interactive instructions may also guide the user through one or more other steps of the process, including activating the thermocycler, inverting the sample analysis receptacle once the sample is loaded, properly loading the sample analysis receptacle in the thermocycler, and/or other instructions.

According to an embodiment, the sample preparation receptacle and the sample analysis receptacle are color-coded or otherwise configured to allow easy differentiation of the tubes. For example, the sample preparation receptacle may be clearly identified by the system as a yellow tube and/or a yellow-capped tube, and the sample analysis receptacle may be clearly identified by the the QR code and plain text labeling on its package. Thus, the instructions can direct the user to properly process the sample from collection to loading of the thermocycler without the user knowing anything else about the tubes or requiring the time to determine which tubes are which. The system also corrects the operator if they try to use the wrong tube for a given step. For example, if an operator scans a Tube B when he should be scanning an assay pouch, the system will alert him or her to the error. This also helps minimize errors in sample preparation, transfer, and analysis.

At step 170 of the method, the sample is analyzed by the thermocycler. According to an embodiment, the sample is analyzed using real-time polymerase chain reaction (PCR), also known as quantitative polymerase chain reaction (qPCR). Accordingly, the thermocycler and/or an associated device comprise a sensor configured to measure fluorescence as the PCR progresses. The sensor may be any sensor capable of receiving signals from the qPCR and communicating either the signal or an interpretation of the signal to a computer or other component of the computerized system. Communication between the sensor and the computer, and between any two or more components of the system, may be via a wired and/or wireless communication connection or network.

According to an embodiment, the thermocycler is configured for multiplex reactions such as a two-channel or duplex assay. The two-channel assay may provide sufficient gap between colors to avoid interaction between the channels. However, many other variations are possible. For example, the thermocycler can be configured for multiplex reactions with more than two colors. The system is only limited by reactions or configurations that prevent adequate detection.

According to an embodiment, the sample analysis receptacle comprises the reagents required for qPCR analysis for the target DNA. For example, the reagents may comprise primers, nucleotides, buffer, a thermo-stable DNA polymerase, and a marker comprised of a fluorophore. If the sample comprises the target organism, and thus the target organism's DNA, target DNA will be amplified and the fluorophore will be excited, allowing the sensor to detect the fluorescence. Thus the system can be used to detect and possibly quantify target DNA in the sample, if the target DNA is present.

According to an embodiment, the cycling program for the thermocycler is configured in whole or in part by the sample and/or the target to be identified within the sample. For example, the identification of the sample analysis receptacle provided to the system in a previous step is stored and is recalled when the system requires directions for the PCR program. Accordingly, the system is preprogrammed with information about particular targets and the associated PCR program needed for that target. This preprogramming can be stored in a database or other memory of the system. The preprogrammed information about the PCR program can include information about temperatures, extension times, cycling numbers, and/or other variables of the PCR program.

According to an embodiment, the interactive instructions may guide the user through the DNA amplification and analysis, including a timer and/or other instructions. For example, the interactive instructions may instruct the user activate the thermocycler, to prepare the computer to receive fluorescence data, to properly load the thermocycler, to time the PCR, and more.

At step 180 of the method, the system analyzes the fluorescence curve obtained from the qPCR and makes a determination regarding the presence or absence of the target in the sample. Accordingly, the system comprises an algorithm that receives raw fluorescence data from the thermal cycler, and uses a curve-fitting application and information about the sample, such as the intended target, to determine whether the fluorescence curve indicates the presence of the target in the analyzed sample. This analysis is performed automatically by the system without requiring manual interpretation by the user. This significantly speeds the process of target identification and/or quantification, and reduces errors in interpretation and analysis by providing objective, repeatable results. The algorithm can be trained or programmed using, for example, experimentally-derived data. For example, samples with targets present, optionally at known amounts, can be analyzed using this process and the resulting fluorescence curves can be used to train the algorithm. Accordingly, the algorithm can be designed to use the known fluorescence curves and/or the data gleaned from the fluorescence curves in order to analyze new fluorescence curves obtained from unknown samples. Each target analyte (pathogen) has its own set of alerting thresholds that have been determined by experimental data.

At step 190 of the method, the system provides a report of the presence or absence determination, from the previous step, to the user. Prior to this step, the system has analyzed the fluorescence curve obtained from the qPCR and has made a determination regarding the presence or absence of the target in the sample. According to one embodiment, the system determines either that a target is present in a sample, or that the target is absent from the sample (or at least not detectable in the sample).

Figure 11:
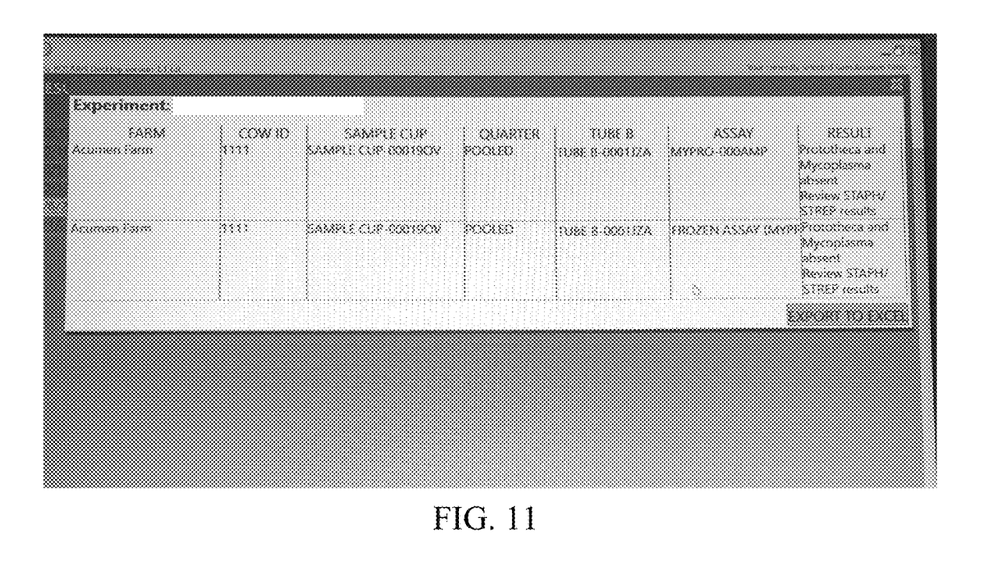
FIG. 11 is a schematic representation of a computerized interactive element of the testing system, in accordance with an embodiment.

Notification may be accomplished via any mechanism that communicates information to a user or another system, either locally or remotely. For example, the system may provide a visual output to the user on a monitor or other screen such as a smartphone, tablet, computer, and/or any other user interface. Referring to FIG. 11, in one embodiment, is a report of samples that have been processed by the system. The report comprises an identification of the location, the sample source (including cow and udder identification), the sample cup, the tube identification, which assay (s) is being performed, and the determination of presence or absence of the target. For example, both samples have reports of an absence of the particular target.

As another option, the system may provide a report to the user via a spreadsheet, a database update, and/or any other method. Indeed, referring again to FIG. 11, the user is able to manually export the information to a spreadsheet ("EXPORT TO EXCEL"), although this may additionally and/or alternatively be an automated process. A notification may also be provided to the user via a text message, audible indicator, email, or any other analog or digital communication method.

According to an embodiment, a report of the presence or absence determination is also or alternatively provided to a facility management system, which may or may not be part of the systems described or otherwise envisioned herein. As yet another example, report of the presence or absence determination is also or alternatively provided to a remote recipient such as a veterinarian, government agency, goods purchaser, and/or some other recipient. In the case of milk testing, for example, the report may be provided to the farm management system and to a veterinarian that services the farm. The system may be configured such that a report is provided to a recipient only in the case of a certain outcome, such as a determination of the presence of a pathogen. This detection may trigger the system, based on predetermined settings or a determination threshold (such as a certain number of detection events either for an individual animal or for a facility), to report information to the remote recipient. The information may comprise the facility location, the affected animal, and/or the target(s) identified in the sample, among other possible information.

Figure 12:
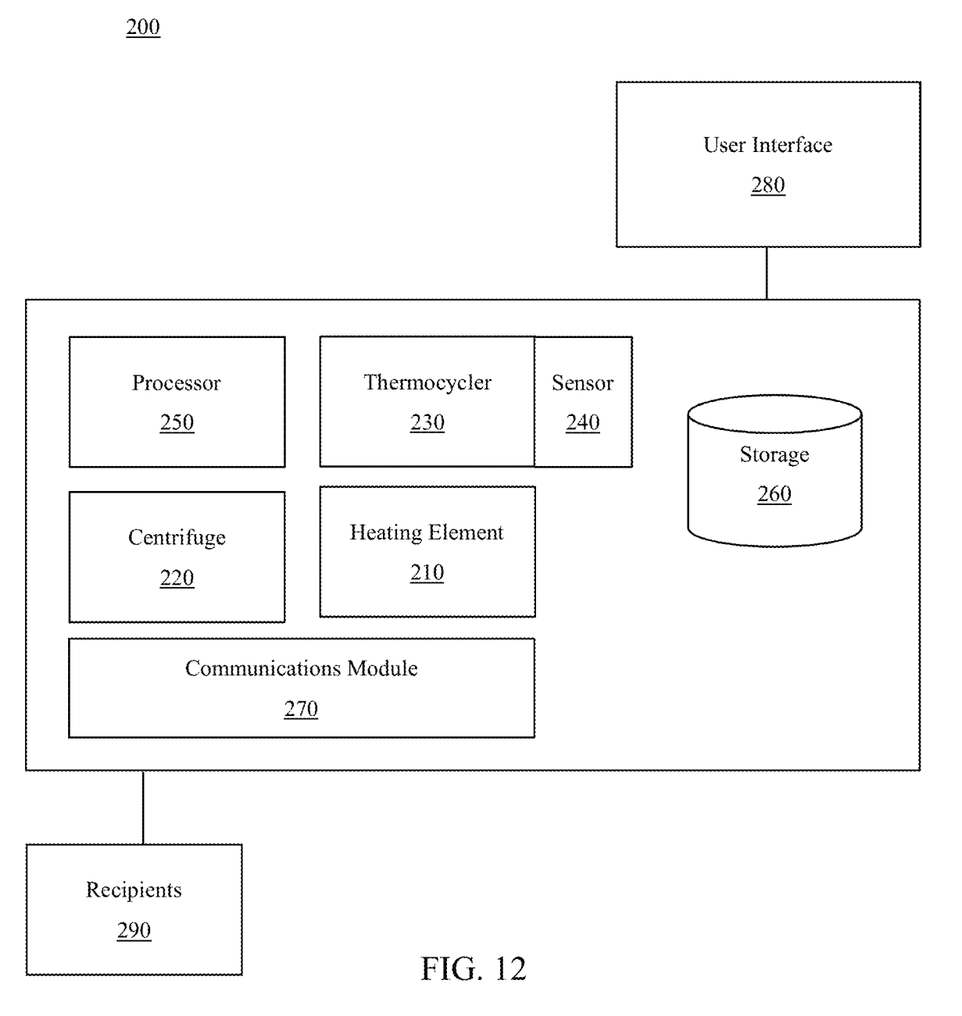
FIG. 12 is a schematic representation of a system for sample preparation and testing, in accordance with an embodiment.

Referring to FIG. 12, in one embodiment, is a guided computerized analysis system 200 for determining the presence or absence of a target in a sample. Although the computerized analysis system is described with reference to specific elements, it is recognized that the system may be implemented with fewer or more elements, and that the description is provided at a level of abstraction. Accordingly, while one or more elements may be described as being separate and/or performing separate steps of the process, it is recognized that a single element may perform multiple steps up to and including all steps of the method.

According to an embodiment, computerized analysis system 200 is a mobile system such that most or all components are easily carried and transferrable from one location to another.

According to an embodiment, computerized analysis system 200 comprises a heating element 210 which may be any mechanism or device suitable to transfer heat to the sample preparation receptacles, such as a heating block or other heating element. As described or otherwise envisioned herein, heating element 210 may be utilized to heat one or more sample preparation receptacles at a first temperature for a first period of time. Heating element 210 may be automated and thus may be regulated by system 200 including activation, timing, temperature setting, and/or deactivation, among other instructions or control.

According to an embodiment, computerized analysis system 200 comprises a centrifuge 220 configured to apply a centrifugal force to the one or more sample preparation receptacles. As described or otherwise envisioned herein, centrifuge 220 may be utilized to apply a centrifugal force to the one or more sample preparation receptacles for a first time period to remove large solids from the suspension. The centrifugal force and the first time period can be designed or selected to maximize successful downstream analysis of the sample. Centrifuge 220 may be automated and thus may be regulated by system 200 including activation, timing, speed setting, and/or deactivation, among other instructions or control.

According to an embodiment, computerized analysis system 200 comprises a thermocycler 230 configured to apply a PCR program to one or more samples. The thermocycler can be any thermocycler capable of applying an amplification program for qPCR. According to an embodiment, the thermocycler comprises or is in communication with a sensor 240 configured to obtain one or more fluorescence curves during the qPCR program. Thus, sensor 240 may be any of a variety of imagers or other sensors capable of detecting the fluorescence emitted by the fluorescent markers utilized in the PCR analysis.

According to an embodiment, computerized analysis system 200 comprises a processor 250 configured to guide the system through sample analysis. Processor 250 may execute, for example, a program or algorithm configured to comprise, perform, or otherwise execute any of the functionality described or otherwise envisioned herein. For example, processor 250 may execute, for example, one or more programs or algorithms to perform any of the functionality described or otherwise envisioned herein. It is understood that one or more of the modules, programs, or algorithms in computer system can be stored in one or more remote memory storage devices or processors in a distributed configuration (not shown). As described or otherwise envisioned herein, processor 250 may be configured to generate or control the automation and other guided steps used in the process. According to an embodiment, processor 250 is a component of a computer specifically configured to interact with the remaining components of computer system 200 via wired and/or wireless communication.

According to an embodiment, computer system 200 comprises or is in communication with storage or memory 260 which is configured to store information about or for the system. For example, storage or memory 260 may store the modules, programs, or algorithms which are executed by processor 250 to perform one or more steps of the method as described or otherwise envisioned herein. As another example, storage or memory 260 may store information about targets and the associated settings for those targets, including the PCR program settings associated with a particular target. As another example, storage or memory 260 may store information provided to the system by the user, including and not limited to all the inputs described or envisioned above. As just a few examples, storage or memory 260 may store user inputs such as a facility identification, an animal identification, a selected target, the results of the qPCR analysis (including the fluorescence curve), and the report of the determination by the system of the presence or absence of the target in the sample.

According to an embodiment, computer system 200 comprises or is in communication with a user interface 280. User interface 280 can present, for example, graphical, textual, and/or other visual information to the user. The user interface may also comprise one or more control features, such as a keyboard, computer mouse, and/or touchscreen, to allow the user to control the system. In one embodiment, the user interface 280 is a graphical user interface and may include a display screen or other type of display. In another embodiment, the user interface 280 is a scanner configured to scan a barcode or other identifier. Many other user interfaces are possible. According to an embodiment, the user may utilize the user interface to input information to the system or receive information from the system. Accordingly, the system may comprise multiple user interfaces which are located with and/or remotely from the other components of system 280. The user interface may enable the user to provide input to the system, including and not limited to all the inputs described or envisioned above. As just a few examples, user inputs provide to the system via user interface 280 may comprise information such as a facility identification, an animal identification, and/or a selected target, among many other types of information.

According to an embodiment, computer system 200 is in communication with one or more recipients 290. For example, the one or more recipients 290 may be any recipient human, system, computer, database, or other recipient which is authorized to receive information about system 200 such as performance information, usage information, and/or report information. For example, a recipient may be a facility manager or management system. As another example, the recipient may be a veterinarian, government agency, goods purchaser, remotely located technical support specialist and/or any other recipient. In the case of milk testing, for example, information about or from system 200 may be provided to the farm management system and to a veterinarian that services the farm. The system may be configured such that information is provided to a recipient only in the case of a certain outcome or other triggering event, such as a test being performed or a determination of the presence of a pathogen.

The computer system 200 may also comprise a wired and/or wireless communications module 270, which can communicate via, for example, wired Wi-Fi, Bluetooth, Ethernet, cellular, IR, radio, or near field communication, among other communication methods. The communications module 270 can communicate with a network, another computer, a wired or wireless device, and/or any other device. For example, the communications module 270 can communicate with or between any components of the system, and/or with the recipient 290, among other destinations either local or remote.

The method and system for semi-automated sample preparation and testing to determine the presence or absence of a target in a sample can be utilized for a wide variety of targets and samples. Although the method and system are described below in regard to specific examples, it is recognized that these are non-limiting examples of the use of the system.

The method and system can be utilized to determine the presence or absence of a target in a milk sample. One important use of the system is to test for the presence or absence of pathogens that cause mastitis in dairy cows, including but not limited to: *Mycoplasma bovis, Mycoplasma* spp., *Prototheca* spp., *Staphylococcus aureus, Staphylococcus* spp., *Streptococcus uberis, Streptococcus* spp., *Escherichia coli* pathogens, *Klebsiella* spp., *Lactococcus* spp., and/or *Pseudomonas* spp., among others. According to an embodiment, the method and system can be utilized to determine the presence or absence of Gram negative bacteria, in which the assay will detect any bacteria within the group of Gram negative bacteria. According to another the method and system can be utilized to determine the presence or absence of Gram positive bacteria, in which the assay will detect any bacteria within the group of Gram positive bacteria.

In addition to mastitis testing in dairy cows, other animal health targets include but are not limited to *Mycobacterium bovis*, the causative agent of bovine tuberculosis, and *Mycobacterium avium* subspecies *paratuberculosis*, the causative agent of Johne's disease in cattle. Furthermore, beyond testing in dairy cows, the systems and methods described or otherwise envisioned herein could include other animal targets such as porcine epidemic diarrhea virus on hog farms, and avian influenza in poultry operations. These and many other targets are possible.

The method and system can be utilized to determine the presence or absence of a target in other settings important to food safety, such as for food safety testing of dairy products such as cheese curds, artisanal cheeses, milk bottling operations. Potential targets in this area include but are not limited to: *Listeria monocytogenes* and/or *Salmonella* spp., among others. These targets are not only relevant to processed dairy products, but are important to virtually all processed foods. Accordingly, the system and/or method may be utilized to detect these and other targets in a variety of matrices such as from environmental monitoring swabs, dry foods such as nuts and spices, and food handling environments such as supermarket deli operations, among many other settings. As yet another example, the system and method may be utilized for water testing for fresh produce where one of the main targets is coliform bacteria, like *E. coli*. Another important target for food safety is the Norovirus.

The method and system can be utilized to determine the presence or absence of other agriculturally important targets such as testing feed for the *Aspergillus* molds that produce aflatoxins, and the *Fusarium* fungi that produce T-2 mycotoxin and vomitoxin, among others.

When implementing one or more of the methods and systems as described herein, the functionality and speed of on-site testing is significantly improved. Since much of the system is automated and/or guides the user through processing steps using visual instructions including test, videos, and/or gifs, the speed of testing is significantly improved. Indeed, as much as 1.5 hours or more of processing time is eliminated for a single test using the methods and systems described or otherwise envisioned herein. Additionally, due to the automation and guidance provided by the system, and due to the computerized tracking of samples and tests by the system, the likelihood of user error is significantly reduced. This isn't possible with current systems which lack automation, guidance, and/or tracking, and which this dramatically increases processing time and the likelihood of errors.

Additionally, the methods and systems described or otherwise envisioned herein provide numerous unexpected advantages over current highly manual methods for testing samples to determine the presence or absence of a target, which require skilled training and use. For example, the pre-heating step of the methods herein provides an unexpected improvement in PCR performance when analyzing the sample. Additionally, the system utilizes prepared receptacles comprising reagents specific to a selected target, which provides both speed and accuracy to the system. Lyophilization of the reagents prolongs shelf-life. Further, because the system analyzes the complex fluorescence curve generated by the PCR and generates a test result without interpretation by a lab technician, the system enables determination of the presence or absence of a target in a sample without requiring skilled training or use. This significantly reduces both time and cost of the system, and provides chain of custody functionality for each step of the method. These and other elements of the methods and systems described or otherwise envisioned herein provide significant improvements over the prior art.

While embodiments of the present invention have been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method for analyzing a sample using a sample analysis system, comprising:
    activating one or more components of the sample analysis system in preparation for a sample of milk, wherein the sample analyses system comprises a heating element, a centrifuge, a thermocycler, an imager, a user interface, and a processor;
    obtaining the sample of milk;
    adding the sample to a sample preparation receptacle;
    heating the sample once in the sample preparation receptacle with the heating element of the sample analysis system at a temperature of 100 degrees Celsius for twenty minutes;
    centrifuging the sample preparation receptacle one time, after heating, for a first period of time using the centrifuge of the sample analysis system;
    transferring at least a portion of the sample, after centrifugation one time, from the sample preparation receptacle to a sample analysis receptacle, the sample analysis receptacle comprising one or more reagents configured for a quantitative polymerase chain reaction specific to a selected target;
    obtaining, via the thermocycler and imager of the sample analysis system, a fluorescence curve during a quantitative polymerase chain reaction;
    analyzing, by the processor of the sample analysis system, the obtained fluorescence curve to determine whether the selected target is present in the sample; and
    reporting, to a user by the user interface of the sample analysis system, the determination whether the selected target is present in the sample;
    wherein the adding, heating, centrifuging and transferring steps are guided by interactive instructions provided to the user via the user interface sample analysis system.

2. The method for analyzing a sample using a sample analysis system of claim 1, wherein the sample preparation receptacle comprises one or more reagents for the sample analysis.

3. The method for analyzing a sample using a sample analysis system of claim 1, further comprising the step of transferring a portion of the sample from the sample preparation receptacle to a reagent-containing tube and mixing to remove additional polymerase chain reaction inhibitors.

4. The method for analyzing a sample using a sample analysis system of claim 1, wherein the instructions comprise a video that demonstrates the action that should be taken by the user.

5. A method for analyzing a sample using a sample analysis system, comprising:
    activating one or more components of the sample analysis system in preparation for a sample of milk, wherein the sample analyses system comprises a heating element, a centrifuge, a thermocycler, an imager, a user interface, a processor; and a memory;
    obtaining the sample of milk potentially and providing the system with information about the sample of milk which is stored in the memory;

adding the sample of milk to a sample preparation receptacle and providing the system with information about the sample analysis receptacle which is stored in the memory;

heating the sample preparation receptacle one time, with the added sample, in the heating element of the sample analysis system at a first temperature of 100 degrees Celsius for twenty minutes;

centrifuging the sample preparation receptacle one time, after heating one time, for a first period of time using the centrifuge of the sample analysis system;

transferring at least a portion of the sample, after centrifugation one time, from the sample preparation receptacle to a sample analysis receptacle, the sample analysis receptacle comprising one or more reagents configured for a quantitative polymerase chain reaction specific to a selected target, and providing the system with information about the sample analysis receptacle which is stored in the memory;

cycling via thermocycler, wherein the identification of the sample analysis receptacle is recalled from the memory and used to determine directions for the polymerase chain reaction program;

obtaining, via the thermocycler and imager of the sample analysis system, a fluorescence curve during a quantitative polymerase chain reaction;

analyzing, by the processor of the sample analysis system, the obtained fluorescence curve to determine whether the selected target is present in the sample; and reporting, to a user by the user interface of the sample analysis system, whether the selected target is present in the sample;

wherein the adding, heating, centrifuging and transferring steps are guided by interactive instructions provided to the user via the user interface sample analysis system.

6. The method for analyzing a sample using a sample analysis system of claim 5, wherein the sample preparation receptacle comprises one or more reagents for the sample analysis.

7. The method for analyzing a sample using a sample analysis system of claim 5, further comprising the step of transferring a portion of the sample from the sample preparation receptacle to a reagent-containing tube and mixing to remove additional polymerase chain reaction inhibitors.

8. The method for analyzing a sample using a sample analysis system of claim 5, wherein the instructions comprise a video that demonstrates the action that should be taken by the user.

9. The method for analyzing a sample using a sample analysis system of claim 5, wherein information about the sample preparation receptacle and the sample analysis receptacle is provided system via a scanner.

10. The method for analyzing a sample using a sample analysis system of claim 9, wherein the sample preparation receptacle comprises a barcode containing information about the receptacle.

* * * * *